(12) United States Patent
Goldminz et al.

(10) Patent No.: US 10,827,940 B2
(45) Date of Patent: Nov. 10, 2020

(54) CONFIGURABLE MULTI-CHANNEL ECG AND EEG MONITOR

(71) Applicant: Asicom Technologies LTD, Nesher (IL)

(72) Inventors: Lavy Goldminz, Haifa (IL); Moshe Chen, Haifa (IL); Yoav Shoham, Haifa (IL)

(73) Assignee: Asicom Technologies LTD, Nesher (IL)

( * ) Notice: Subject to any disclaimer, the term of this patent is extended or adjusted under 35 U.S.C. 154(b) by 117 days.

(21) Appl. No.: 15/757,376

(22) PCT Filed: Sep. 4, 2016

(86) PCT No.: PCT/IL2016/050973
§ 371 (c)(1),
(2) Date: Mar. 5, 2018

(87) PCT Pub. No.: WO2017/037721
PCT Pub. Date: Mar. 9, 2017

(65) Prior Publication Data
US 2018/0256063 A1 Sep. 13, 2018

Related U.S. Application Data

(60) Provisional application No. 62/214,988, filed on Sep. 6, 2015.

(51) Int. Cl.
*A61B 5/0428* (2006.01)
*A61B 5/00* (2006.01)
*A61B 5/04* (2006.01)
*A61B 5/042* (2006.01)
*A61B 5/0476* (2006.01)

(52) U.S. Cl.
CPC ........ *A61B 5/04288* (2013.01); *A61B 5/0006* (2013.01); *A61B 5/04004* (2013.01); *A61B 5/0422* (2013.01); *A61B 5/0476* (2013.01); *A61B 5/7225* (2013.01)

(58) Field of Classification Search
CPC .............. A61B 5/04288; A61B 5/0006; A61B 5/04004; A61B 5/0422; A61B 5/0476; A61B 5/7225
See application file for complete search history.

*Primary Examiner* — Paula J Stice
(74) *Attorney, Agent, or Firm* — Reches Patent

(57) ABSTRACT

A monitor that includes multiple detection channels having multiple input ports for receiving a group of electrical physiological signals from a person; wherein multiple switching circuits of the monitor are configured according to a first configuration when the monitor operates in a first mode, thereby causing each electrical physiological signal of the group to be processed by up to a single selected detection channel of the multiple detection channels; wherein the multiple switching circuits of the monitor are configured according to a second configuration when the monitor operates in a second mode thereby causing one or more of the multiple electrical physiological signals of the group to be processed by at least two selected detection channels of the multiple detection channels.

18 Claims, 10 Drawing Sheets

CONFIGURABLE MULTI-CHANNEL ECG AND EEG MONITOR

BACKGROUND OF THE INVENTION

Various monitoring procedures such as electroencephalogram (EEG) and electrocardiogram (ECG) monitoring procedures are implemented using monitors that include increasing numbers of detection channel.

A monitor may include multiple electrodes.

The number of catheter electrodes in intra-cardiac ECG monitors and in Wearable EEG monitors is constantly increasing.

Each catheter electrode is connected to a different detection channel. Each detection channel may process only a single electrical physiological signal.

FIG. 1 illustrates a prior art monitor 20 that monitors a person 10. The monitor 20 includes an intracardiac catheter 30 that includes multiple (N) conductors 32(1)-32(N). Each conductor electrically connected to an electrode and each receives a single ECG signal.

Each detection channel of the N detection channels 80(1)-80(N) of monitor 20 may receive up to a single ECG signal (and a reference WCT signal generated by WCT reference circuit 70) and process only up to a single ECG signal.

A display 90 displays multiple (N) ECG waveforms 92(1)-92(N)—one per each ECG signal.

Each detection channel has its own analog signal conditioning circuit. Each analog conditioning channel amplifies and filters the signals received by the catheter tip.

In modern monitors the output of the analog signal conditioning circuit is converted to digital signals (also referred to as intermediate digital signals) by analog to digital converters (ADC) for further digital signal processing.

The increasing number of electrodes is used to obtain higher resolution and a more detailed electric activity map of an organ of the person. As a result a more complex multi-channel electronic (Analog and Digital) and software is required.

In an environment of a large number of electrodes a fine detailed ECG (or EEG) line originated from a specific electrode is required to help the user to reach more accurate medical decisions.

Noise generated by detection channels (for example—noise introduced by the signal conditioning circuits and/or the ADC) is the main obstacle to obtain a clear ECG (or EEG) picture.

The intra-cardiac ECG system (as in Wearable EEG system) must enable the user to focus on each of the many detection channels and to extract a high quality signal from the selected detection channel.

Each detection channel connected to each electrode must be realized by low noise circuitry.

Building a low noise multi-channel device in which each detection channel is good enough to view the fine details needed is expensive and power inefficient.

SUMMARY OF THE INVENTION

According to an embodiment of the invention there may be provided a monitor that may include multiple detection channels having multiple input ports for receiving a group of electrical physiological signals from a person; wherein multiple switching circuits of the monitor may be configured according to a first configuration when the monitor operates in a first mode, thereby causing each electrical physiological signal of the group to be processed by up to a single selected detection channel of the multiple detection channels; wherein the multiple switching circuits of the monitor may be configured according to a second configuration when the monitor operates in a second mode thereby causing one or more of the multiple electrical physiological signals of the group to be processed by at least two selected detection channels of the multiple detection channels.

The multiple switching circuits may be coupled to multiple analog signal conditioning circuits of the multiple detection channels.

The multiple switching circuits belong to multiple analog signal conditioning circuits of the multiple detection channels.

The switching circuits that belong to different detection channels may be configured to output different electrical physiological signals when the monitor operates in the first mode; and wherein a plurality of switching circuits that belong to a plurality of different selected detection channels may be configured to output a same electrical physiological signal when the monitor operates in the second mode.

The at least two switching circuits may belong to neighboring detection channels.

The at least two switching circuits may belong to more than two detection channels.

The each switching circuit may include three or more inputs for receiving three or more electrical physiological signals of the group.

The each switching circuit is positioned between different analog components of the analog conditioning circuit.

The each switching circuit is a first analog component of the analog conditioning circuit.

The each switching circuit is a last analog component of the analog conditioning circuit.

The each switching circuit is followed by an analog amplifier of the analog conditioning circuit; wherein the analog amplifier is also fed by a reference signal.

The multiple detection channels comprise multiple analog conditioning circuits that may be followed by multiple analog to digital converters for converting multiple analog output signals of the multiple analog conditioning circuits to multiple intermediate digital signals; wherein the multiple analog to digital converters may be followed by a digital manipulator; wherein the digital manipulator is prevented from adding intermediate digital signals from analog conditioning circuits of different selected detection channels when the monitor operates in a first mode; wherein the digital manipulator may be configured to add intermediate digital signals from analog conditioning circuits of the at least two selected detection channels when the monitor operates in the second mode.

The digital manipulator may include a digital manipulation circuit per each detection channel; wherein each digital manipulation circuit is coupled to a set of digital to analog converters of a set of detection channels.

The a digital manipulation circuit of a given detection channel that belongs to a given set of detection channels may include: a plurality of IO interfaces, each IO interface is coupled to a digital manipulation circuit of another detection channel of the given set; an adder that has (a) a first input that is coupled to the analog to digital circuit of the given detection channel, (b) an IO interface for each other detection channel of the set, wherein each IO interface is coupled to a digital manipulation circuit of another detection channel of the set, and (c) an adder output; an output circuit for outputting a digital manipulation circuit output signal;

wherein the output circuit is coupled to the adder output and to each one of the plurality of IO interfaces.

The digital manipulator is followed by a decision module for making decisions based upon output signals of the detection channels. The decision module may be a hardware processor or may hosted or executed by the hardware processor, may be a part of a gaming device, of a wearable device, and the like.

The monitor further may include a display for displaying multiple output signals of the multiple detection channels.

The display may be configured to display an aggregate signal that represents an outcome of the processing each one of the one or more of the multiple electrical physiological signals by the at least two selected detection channels of the multiple detection channels.

The group of physiological signals may be electrocardiogram (ECG) signals.

The group of physiological signals may be electroencephalogram (EEG) signals.

The monitor may include a controller that may be configured to determine an operational mode of the monitor.

According to an embodiment of the invention there may be provided a method for monitoring a person, the method may include receiving, by input ports of a monitor, a group of electrical physiological signals from a person; configuring multiple switching circuits of the monitor according to a first configuration when the monitor operates in a first mode, thereby causing each electrical physiological signal of the group to be processed by up to a single selected detection channel of multiple detection channels of the monitor; configuring multiple switching circuit of the monitor according to a second configuration when the monitor operates in a second mode, thereby causing one or more of the multiple electrical physiological signals of the group to be processed by at least two selected detection channels of the multiple detection channels.

According to an embodiment of the invention there may be provided a non-transitory computer readable medium that may store instructions that once executed by a monitor cause the monitor to: configure multiple switching circuits of the monitor according to a first configuration when the monitor operates in a first mode, thereby causing each electrical physiological signal of a group of electrical physiological signals received from a person to be processed by up to a single selected detection channel of multiple detection channels of the monitor; configuring multiple switching circuit of the monitor according to a second configuration when the monitor operates in a second mode, thereby causing one or more of the multiple electrical physiological signals of the group to be processed by at least two selected detection channels of the multiple detection channels.

According to an embodiment of the invention there is provided a monitor that includes an adaptor for directing an electrical physiological signal to multiple detection channels and an adder or a redistribution circuit for adding the outputs of the multiple detection channels to provide an enhanced signal of better quality. The adaptor and/or the adder may be static or configurable. The adaptor may precede the detection channels, and may be included in the input physiological interface.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

Figure 1:
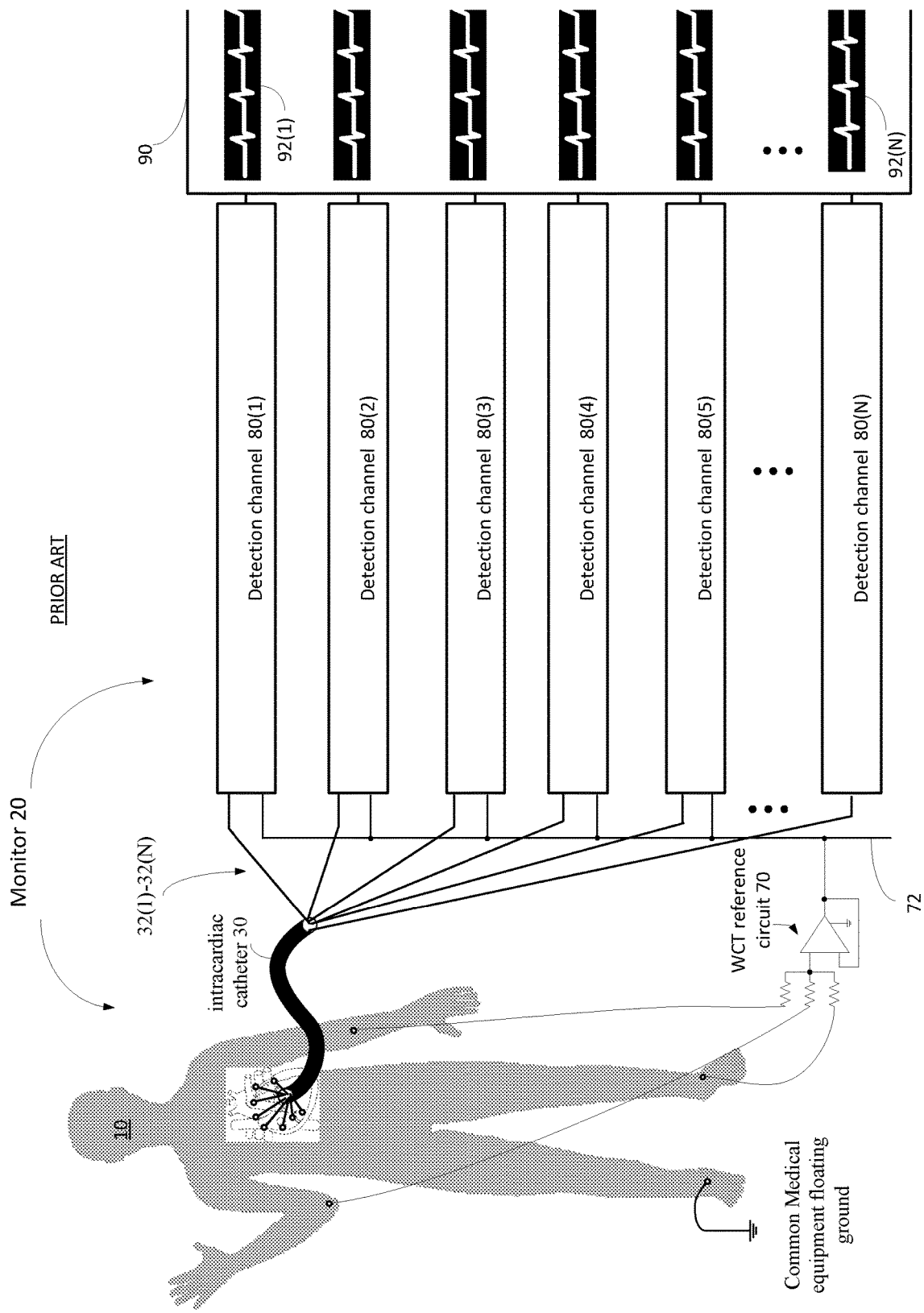
FIG. 1 illustrates a person and a prior art monitor.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE DRAWINGS

According to an embodiment of the invention there may be provided a monitor that may include multiple detection channels, each detection channel includes an analog conditioning circuit for amplifying and filtering electrical physiological signals received by multiple electrodes such as intra body electrodes for intra-cardiac ECG or electrodes embedded in wearable EEG devices.

The monitor may be a health monitor or may monitor a person for other reasons (not related to health). For example the monitor may be used to generate commands or decisions based upon monitored electrical physiological signals of a person. For example, the monitor may be a wearable EEG device that monitors electrical physiological signals for gaming purposes, controlling electronic devices, assisting in disable person to control devices and/or to communicate, and the like.

Each detection channel may exhibit high input impedance.

The monitor may measure a signal provided by a single electrode or by a plurality of channels in parallel.

In order to measure a signal by the plurality of channels the monitor is arranged to (a) distribute signals between the multiple detection channels and (b) to add processed signals from the multiple detection channels.

The distribution may be performed in the analog domain while the redistribution may be performed in the analog domain or in the digital domain. Performing the adding in the digital domain may assist in compensating noises and/or inaccuracies resulting from the analog to digital conversion.

Figure 2:
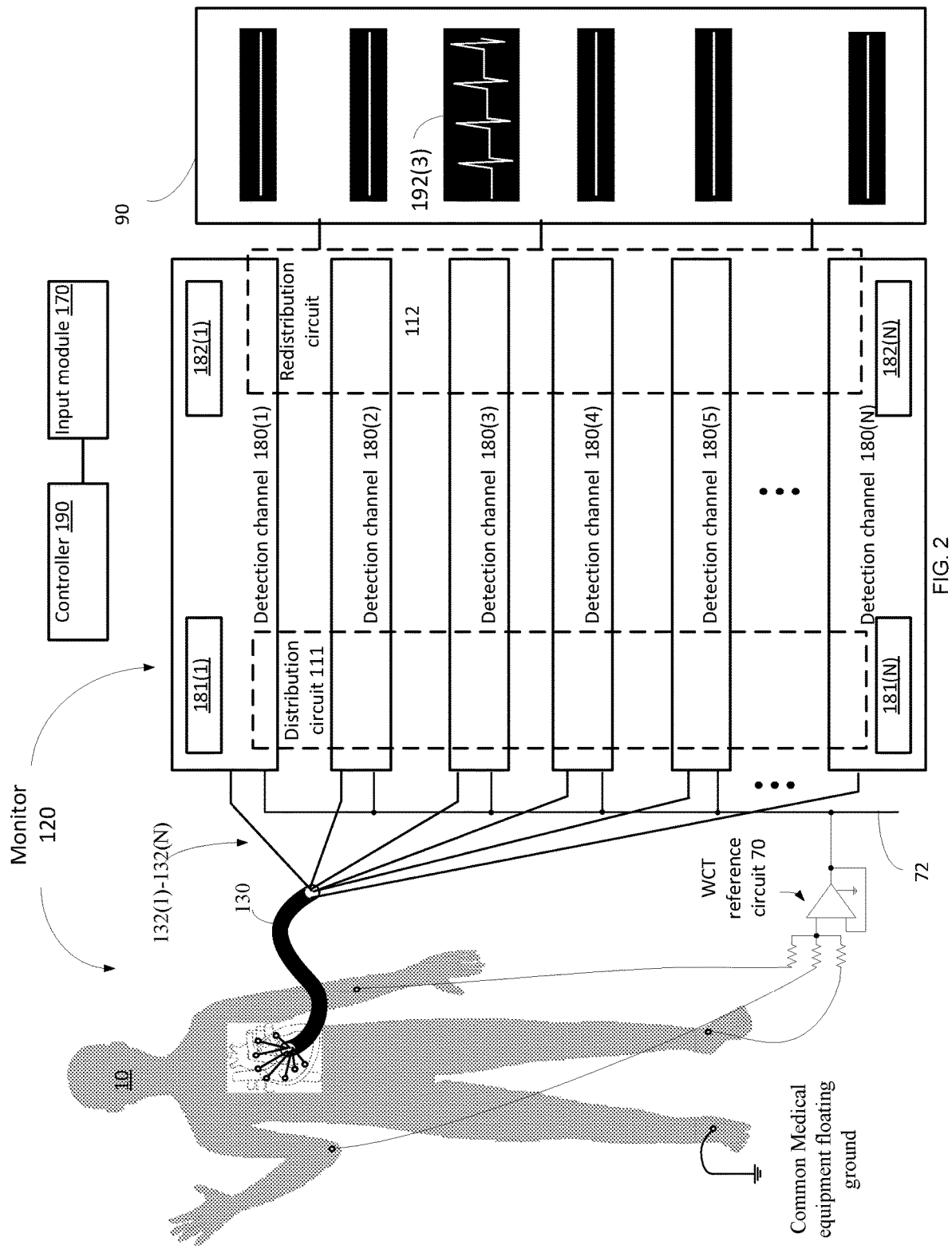
FIG. 2 illustrates a monitor according to an embodiment of the invention.

FIG. 2 illustrates a monitor 120 according to an embodiment of the invention.

Monitor 120 includes a physiological input interface 130, multiple (N) detection channels 180(1)-180(N), a distribution circuit 111, a redistribution circuit 112, a display 90, WCT reference circuit 70, controller 190 and input module 170.

Controller 190 controls the operation of the monitor 120 and especially controls the configuration of distribution circuit 111 and redistribution circuit 112.

N is a positive integer that exceeds three.

Input module 170 may be a keyboard, a mouse, a touch screen (that may or may not be display 90) for receiving instructions from a user of the monitor 120.

The user may instruct monitor 120 to operate in a first mode (also referred as to a serial mode) in which each detection channel operates independently from each other and any electrical physiological signal is processed by up to a single detection channel.

The user may instruct monitor 120 to operate in a second mode during which at least one electrical physiological signal is processed by two or more detection channels. See, for example, FIGS. 4, 5 and 6.

Physiological input interface 130 includes multiple conductors 132(1)-132(N) that are coupled between N electrodes that contact person 10 and the N detection channels 180(1)-180(N).

It is noted that any one of the electrodes and/or the conductors may be disconnected (not be used). Additionally or alternatively, the monitor 120 may include unused electrodes and conductors that are not illustrated in FIG. 2.

In FIG. 2 the physiological input interface 130 is illustrated as being an intercardiac catheter but this is not necessarily so. For example (see FIG. 3) the physiological input interface may be a set of EEG conductors.

Each one of the N detection channels may include an analog signal conditioning circuit, an ADC and a digital processing circuit.

For simplicity of explanation only the first and N'th detection channels are illustrated as including an analog signal conditioning circuit (181(1) and 181(N) respectively) and a digital processing circuit (182(1) and 182(N) respectively).

Each one of the detection channels may have high input impedance. The distribution of an electrical physiological signal between two or more detection channels may not distort (or only insignificantly distort) the distributed electrical physiological signals.

The multiple detection channels (or at least some of the N detection channels) may be coupled to in parallel to each other by (a) distribution circuit 111 for distributing signals between the detection channels and (b) by redistribution circuit 112 for adding processed signals from the plurality of detection channels.

Figure 4:
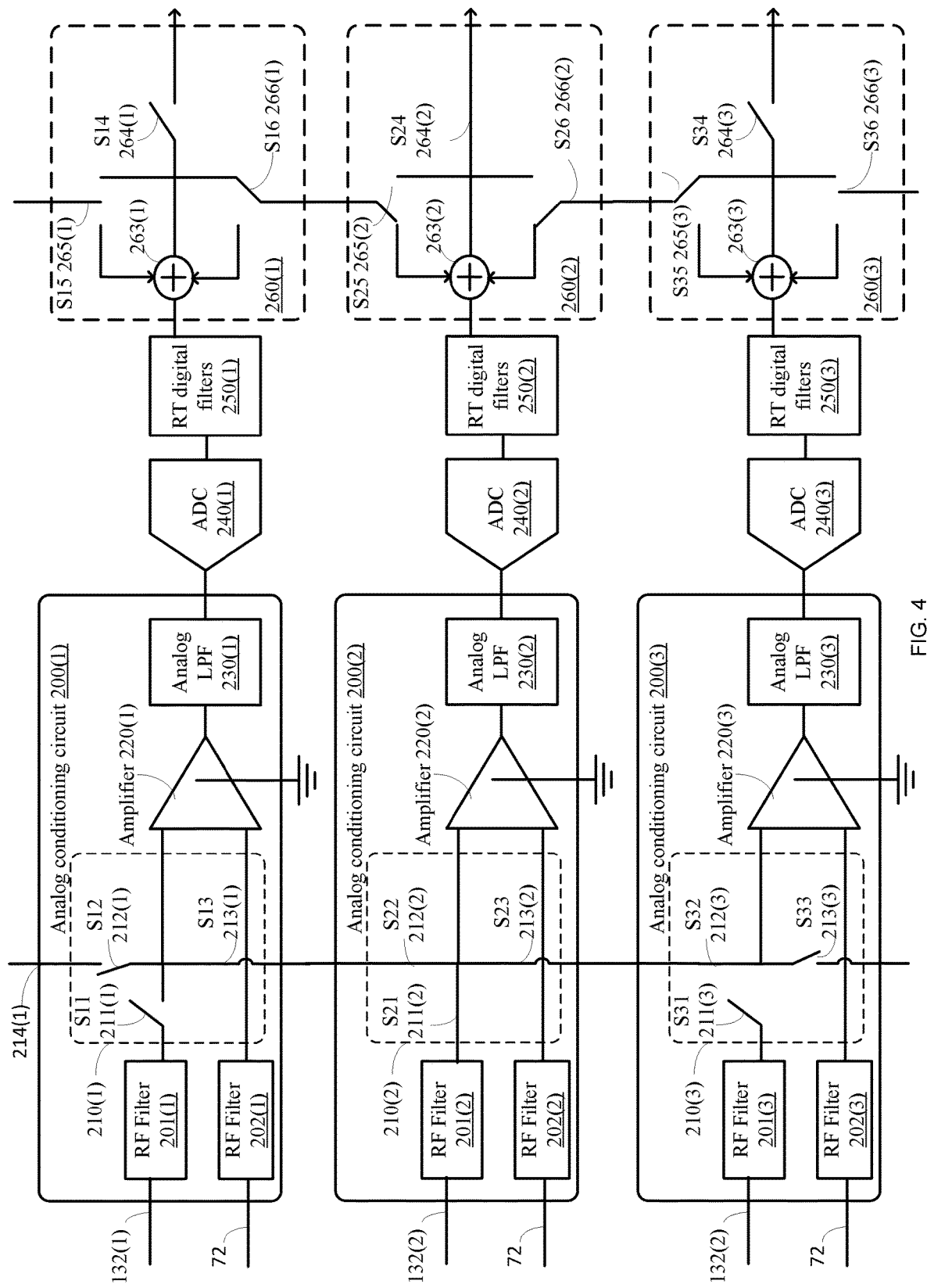
FIG. 4 illustrates detection channels according to an embodiment of the invention.
Figure 5:
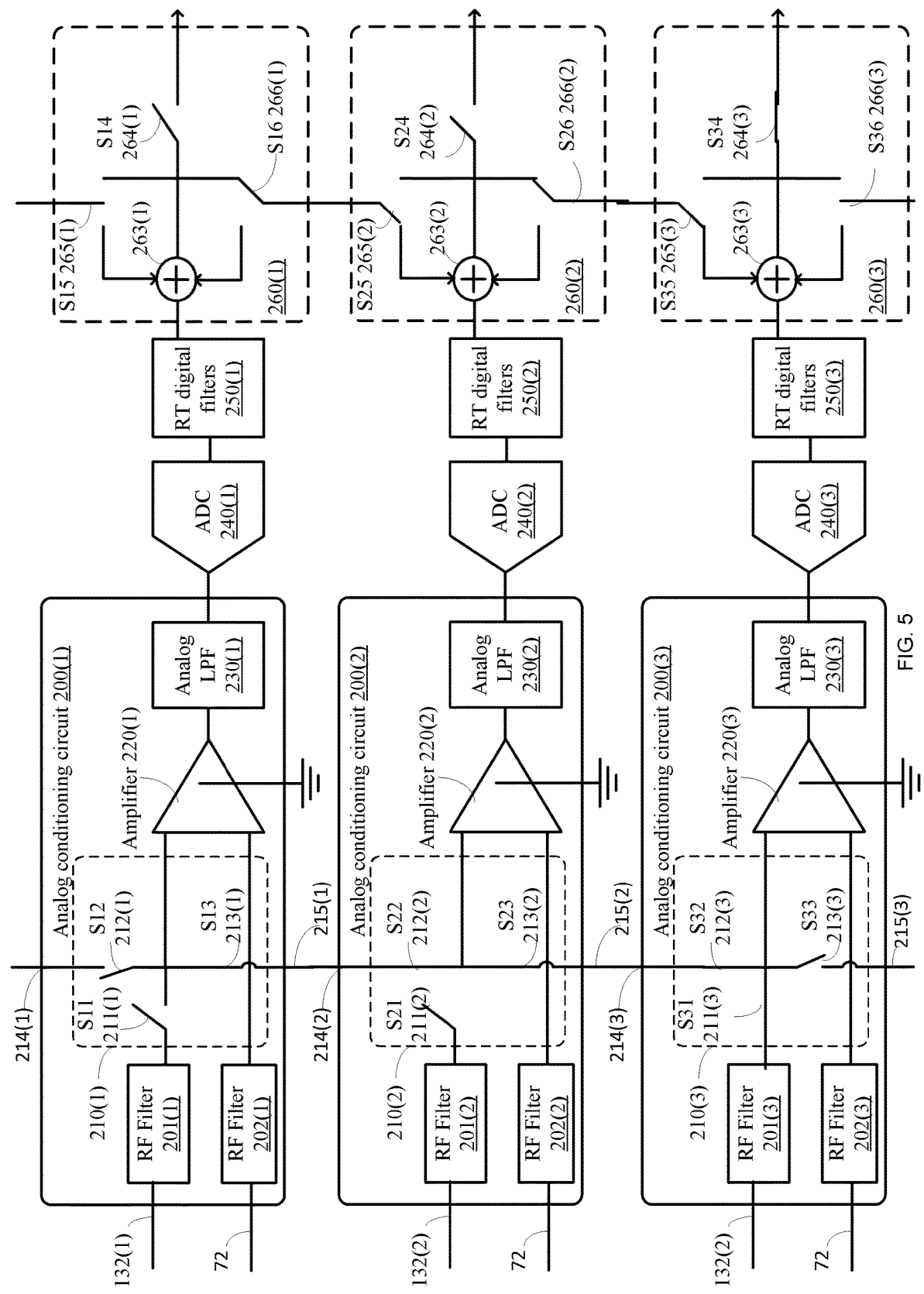
FIG. 5 illustrates detection channels according to an embodiment of the invention.
Figure 6:
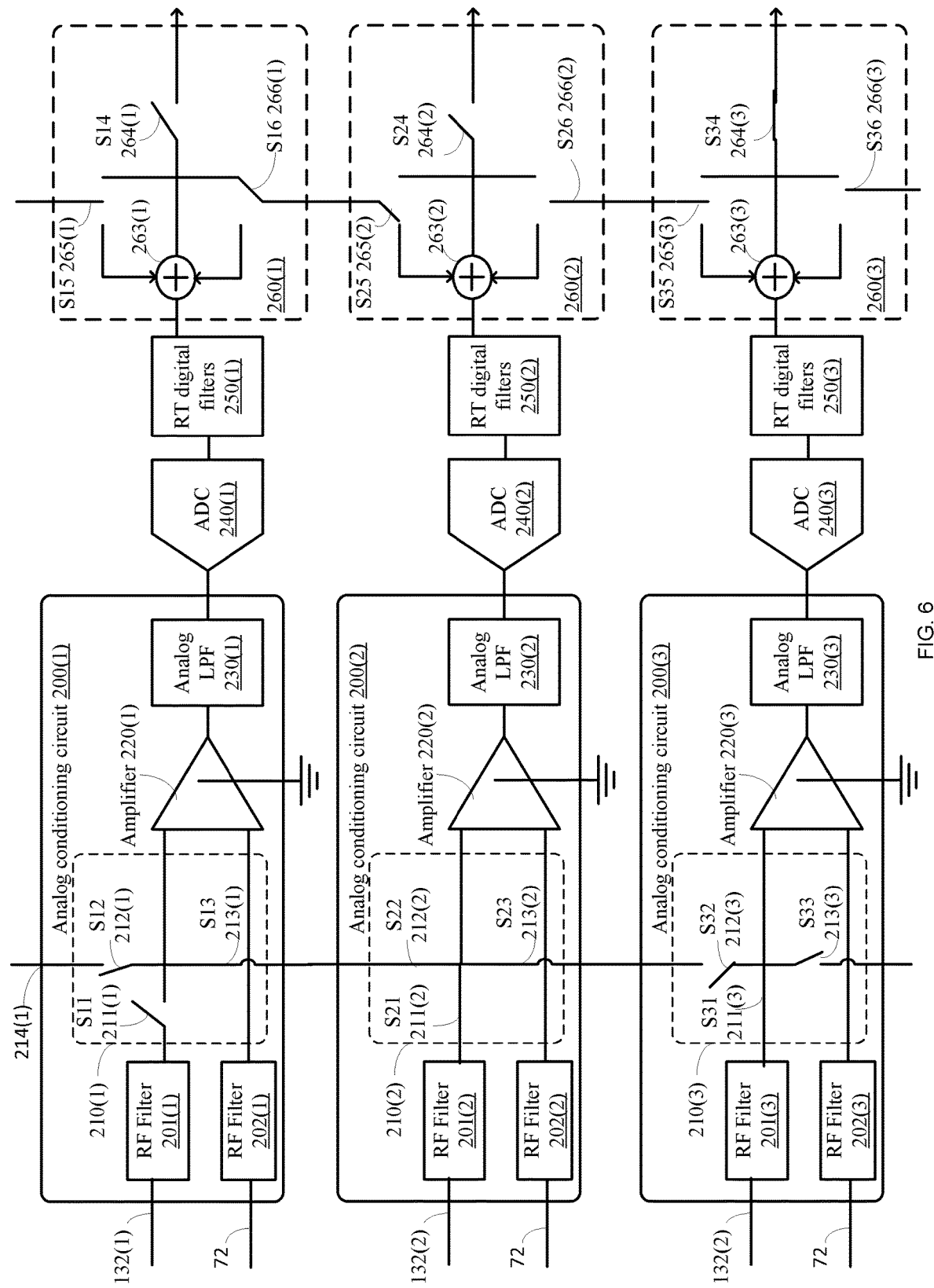
FIG. 6 illustrates detection channels according to an embodiment of the invention.

The distributed signals may include the electrical physiological signals provided by the physiological input interface 130 or partially processed electrical physiological signals (for example filtered electrical physiological signals). In FIGS. 4-6 the distributed signals are already high pass filtered before being distributed.

The processed signals that are summed by the redistribution circuit 112 may be digitally processed signals, analog processed signal and the like.

The distribution circuit 111 may distribute any electrical physiological signal to any detection channel or may distribute any electrical physiological signal to a subset of the detection channels.

The number of parallelly connected channels may be dynamic (between two detection channels up to all of the multiple detection channels) and may be determined (by the user) according to the resolution fine details the user wants to observe in the sensed ECG or EEG signal.

According to an embodiment of the invention some of the detection channels may operate in a "serial" manner (single detection channel per electrical physiological signal) while other detection channels may work in parallel to each other (and process the same electrical physiological signal). See, for example, FIG. 6.

The user may request to focus on two or more electrical physiological signals at the same time and there may be multiple groups of detection channels—each group operates in parallel on one of these focused electrical physiological signals.

FIG. 2 also illustrates an ECG waveform 192(2) that is obtained by summing (or applying a weighted sum) on output signals of two or more detection channels.

Figure 3:
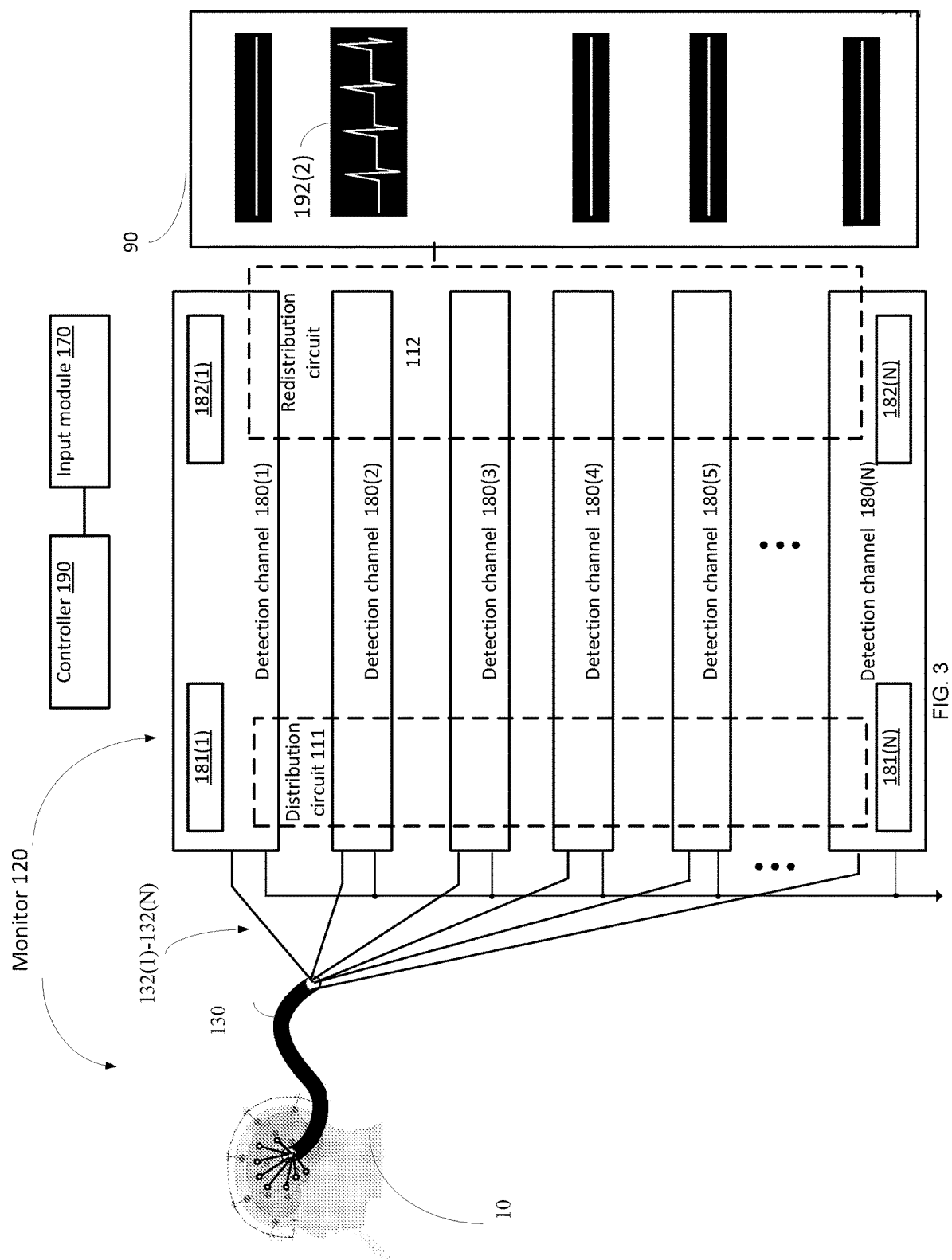
FIG. 3 illustrates a monitor according to an embodiment of the invention.

FIG. 3 illustrates the monitor 120 as performing an EEG measurement.

FIG. 4 illustrates three detection channels 180(1), 180(2) and 180(3) and a switching circuit of monitor 120 according to an embodiment of the invention.

It is assumed, for simplicity of explanation, that the three detection channels operate in parallel to process the electrical physiological signal received from second conductor 132(2).

Each detection channel includes a pair of radio frequency (RF) filters.

First detection channel 180(1) includes (a) a first RF filter 201(1) for filtering the electrical physiological signal received from first conductor 132(1) to provide a first RF filtered signal and (b) a first reference RF filter 202(1) for filtering reference signal 72.

Second detection channel 180(2) includes (a) a second RF filter 201(2) for filtering the electrical physiological signal received from second conductor 132(2) to provide a second RF filtered signal and (b) a second reference RF filter 202(2) for filtering reference signal 72.

Third detection channel 180(3) includes (a) a third RF filter 201(3) for filtering the electrical physiological signal received from third conductor 132(3) to provide a third RF filtered signal and (b) a third reference RF filter 202(3) for filtering reference signal 72.

The pair of RF filters are followed by an input switching unit that may be a part of the distribution circuit.

Each input switching circuit includes a main input, a top input and a bottom input. The main input is used for receiving a main filtered RF signal—the filtered RF signal from the RF filter that belong to the same detection channel as the input switching circuit.

The terms "top", "above", "bottom" and "below" are used to distinguish between two detection channels that may be coupled to a given detection channel. These terms refer to an arbitrary order of the detection channels. For example—second detection channel is above third detection channel and below first detection channels.

The top input is used for receiving a top filtered RF signal from an RF filter that belongs to a detection channel that is "above" the detection channel of the input switching circuit.

The bottom input is used for receiving a bottom filtered RF signal from an RF filter that belongs to a detection channel that is "below" the detection channel of the input switching circuit.

Each input switching circuit may select which filtered RF signal (out of the main filtered RF signal, the top filtered RF signal and the bottom filtered RF signal) to output. In FIG. 4 each input switching circuit include a main switch, a top switch and a bottom switch for performing the selection.

First detection channel 180(1) includes first input switching circuit 210(1) that includes a first main input, first top input 214(1), first bottom input 215(1), first main switch S11 211(1), first top switch S12 212(1) and first bottom switch S13 213(1).

Second detection channel 180(2) includes second input switching circuit 210(2) that includes a second main input, second top input 214(2), second bottom input 215(2), second main switch S21 211(2), second top switch S22 212(2) and second bottom switch S23 213(2).

Third detection channel 180(3) includes third input switching circuit 210(3) that includes a third main input, third top input 214(3), third bottom input 215(3), third main switch S31 211(3), third top switch S32 212(3) and third bottom switch S33 213(3).

Each input switching circuit includes an amplifier (such as a differential amplifier) that receives a filtered RF reference signal and an output signal of the input switching circuit.

First till third detection channels 180(1), 180(2) and 180(3) include first, second and third amplifiers 220(1), 220(2) and 220(3) respectively.

In FIG. 4 it is assumed that the electrical physiological signal from the second conductor 132(2) is processed by the three detection channels.

Table 1 illustrates the state of various switches. Open (disconnected) is represented by 0 and closed (connected) is represented by 1.

TABLE 1

| S11 | S12 | S13 | S21 | S22 | S23 | S31 | S22 | S23 |
|-----|-----|-----|-----|-----|-----|-----|-----|-----|
| 0   | 0   | 1   | 1   | 1   | 1   | 0   | 1   | 0   |

In each detection channel the amplifier is followed by an analog low pass filter (LPF). The pair of input RF signals, the input switching circuit, the amplifier and the analog LPF form an analog conditioning circuit.

First till third detection channels 180(1), 180(2) and 180(3) include first analog LPF 230(1), second analog LPF 230(2) and third analog LPF 230(3) respectively.

First detection channel 180(1) includes a first analog conditioning circuit 200(1). First analog conditioning circuit 200(1) includes first RF filter 201(1), first reference RF filter 202(1), first input switching circuit 210(1), first amplifier 220(1) and first analog LPF 230(1).

The second detection channel 180(2) includes a second analog conditioning circuit 200(2). Second analog conditioning circuit 200(2) includes second RF filter 201(2), second reference RF filter 202(2), second input switching circuit 210(2), second amplifier 220(2) and second analog LPF 230(2).

The third detection channel 180(3) includes a third analog conditioning circuit 200(3). Third analog conditioning circuit 200(3) includes third RF filter 201(3), third reference RF filter 202(3), third input switching circuit 210(3), third amplifier 220(3) and third analog LPF 230(3).

In each detection channel the analog conditioning circuit is followed by an ADC that is followed by real time (RT) digital filters. The RT digital filters are followed by an output switching circuit that belongs to the redistribution circuit.

Each output switching circuit includes a main input, a top switch, a bottom switch and an output switch.

The main input is used for receiving a main digitally filtered signal—the digitally filtered signal from the RT digital filters that belong to the same detection channel as the output switching circuit.

The output switch is used to determine whether an output signal of the adder is provided to a display and be displayed by the display.

The top switch may be in an input position, an open position and an output position.

When in an input position the top switch is used for feeding the adder (of the output switching circuit of the top switch) with signals from an output switching circuit of a top detection channel that is "above" the detection channel of the output switching circuit.

When in an output position the top switch is used for feeding the output switching circuit of the top detection channel with an output of the adder (of the output switching circuit of the top switch).

When in an open position the output switching circuits of the top detection channel and of the top switch are disconnected.

The bottom switch may be in an input position, an open position and an output position.

When in an input position the bottom switch is used for feeding the adder (of the output switching circuit of the bottom switch) with signals from an output switching circuit of a bottom detection channel that is "below" the detection channel of the output switching circuit.

When in an output position the bottom switch is used for feeding the output switching circuit of the bottom detection channel with an output of the adder (of the output switching circuit of the bottom switch).

When in an open position the output switching circuits of the bottom detection channel and of the bottom switch are disconnected.

Referring to FIG. 4—first detection channel includes first output switching circuit 260(1). First output switching circuit 260(1) includes first adder 263(1), first top switch S15 265(1), first bottom switch S16 266(1) and first output switch S14 264(1). First top switch S15 265(1) and first bottom switch S16 266(1) are in an input mode when they are connected to an input of the adder (oriented to the left), are in an output mode when they are connected to the output of the adder (oriented to the right) or disconnected (vertical).

Second detection channel includes second output switching circuit 260(2). Second output switching circuit 260(2) includes second adder 263(2), second top switch S15 265(2), second bottom switch S16 266(2) and second output switch S14 264(2). Second top switch S15 265(2) and second bottom switch S16 266(2) are in an input mode when they are connected to an input of the adder (oriented to the left), are in an output mode when they are connected to the output of the adder (oriented to the right) or disconnected (vertical).

Third detection channel include third output switching circuit 260(3). Third output switching circuit 260(3) includes third adder 263(3), third top switch S15 265(3), third bottom switch S16 266(3) and third output switch S14 264(3). Third top switch S15 265(3) and third bottom switch S16 266(3) are in an input mode when they are connected to an input of the adder (oriented to the left), are in an output mode when they are connected to the output of the adder (oriented to the right) or disconnected (vertical).

Because there are more than two detection channels then signals from another detection channel may be digitally filtered signal that was only processed by the other detection signals or may be a sum of digitally filtered signals that were processed by two or more other detection channels.

In FIG. 4 it is assumed that the second output switching circuit sums the output signals from the first and third output switching circuits and outputs it output signal to the display.

Table 2 illustrates the state of various switches. Input position is represented by In, output position is represented by Out, disconnected is represented by 0 and connected is represented by 1.

TABLE 2

| S15 | S16 | S14 | S25 | S26 | S24 | S35 | S36 | S34 |
|---|---|---|---|---|---|---|---|---|
| 0 | Out | 0 | In | In | 1 | Out | 0 | 0 |

FIG. 5 illustrates three detection channels 180(1), 180(2) and 180(3) and a switching circuit of monitor 120 according to an embodiment of the invention.

It is assumed, for simplicity of explanation, that the three detection channels operate in parallel to process the electrical physiological signal received from third conductor 132(3).

Table 3 illustrates the state of various switches. Open (disconnected) is represented by 0 and closed (connected) is represented by 1.

TABLE 3

| S11 | S12 | S13 | S21 | S22 | S23 | S31 | S22 | S23 |
|---|---|---|---|---|---|---|---|---|
| 0 | 0 | 1 | 0 | 1 | 1 | 1 | 1 | 0 |

Table 4 illustrates the state of various switches. Input position is represented by In, output position is represented by Out, disconnected is represented by 0 and connected is represented by 1.

TABLE 4

| S15 | S16 | S14 | S25 | S26 | S24 | S35 | S36 | S34 |
|---|---|---|---|---|---|---|---|---|
| 0 | Out | 0 | In | Out | 0 | In | 0 | 1 |

FIG. 6 illustrates three detection channels 180(1), 180(2) and 180(3) and a switching circuit of monitor 120 according to an embodiment of the invention.

It is assumed, for simplicity of explanation, that the first two detection channels operate in parallel to process the electrical physiological signal received from second conductor 132(2) and that the third detection signal operated in a serial manner to process the electrical physiological signal received from first conductor 132(1).

Table 5 illustrates the state of various switches. Open (disconnected) is represented by 0 and closed (connected) is represented by 1.

TABLE 5

| S11 | S12 | S13 | S21 | S22 | S23 | S31 | S22 | S23 |
|---|---|---|---|---|---|---|---|---|
| 0 | 0 | 1 | 1 | 1 | 1 | 1 | 0 | 0 |

Table 6 illustrates the state of various switches. Input position is represented by In, output position is represented by Out, disconnected is represented by 0 and connected is represented by 1.

TABLE 6

| S15 | S16 | S14 | S25 | S26 | S24 | S35 | S36 | S34 |
|---|---|---|---|---|---|---|---|---|
| 0 | Out | 0 | In | Out | 0 | 0 | 0 | 1 |

The top and bottom switches of the output switching circuit may be included in or replaced by a top IO interface and a bottom IO interface.

Figure 7:
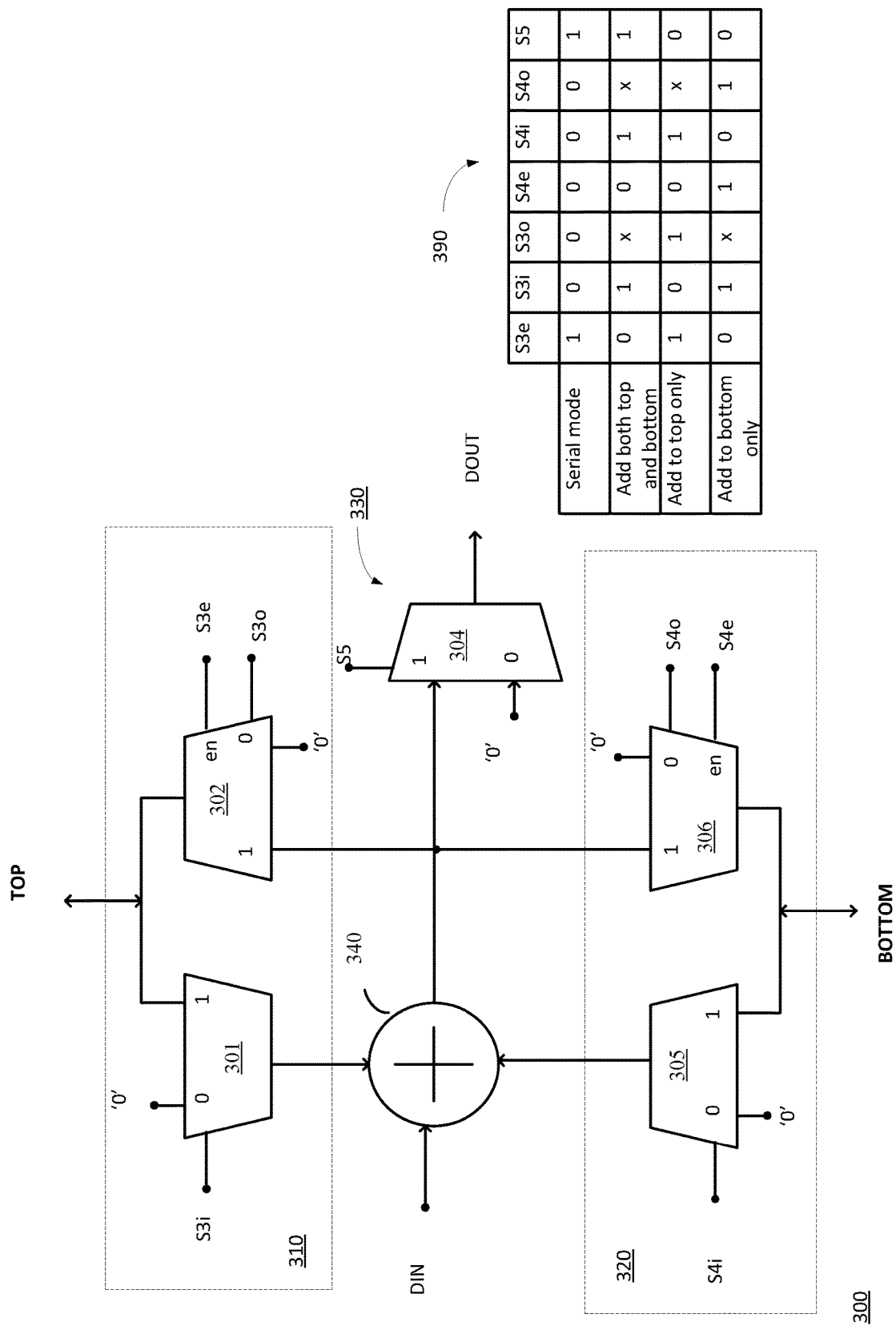
FIG. 7 illustrates an output switching circuit according to an embodiment of the invention.

FIG. 7 illustrates an output switching circuit 300 according to an embodiment of the invention.

Output switching circuit 300 includes adder 340, top switch 310, bottom switch 320 and output switch 330.

Top switch 310 includes a top input multiplexer 301 and a top output multiplexer 302.

Bottom switch 302 includes a top input multiplexer 301 and a top output multiplexer 302.

Output switch 330 includes output multiplexer 304.

The top input multiplexer 301 has a first input that is fed by zero, a second input that is connected to a top output switching circuit and is controlled by a select signal S3$i$ for selecting between the first and second inputs. The output of the top input multiplexer 301 is connected to an input of adder 340.

The bottom input multiplexer 305 has a first input that is fed by zero, a second input that is connected to a bottom output switching circuit and is controlled by a select signal S4$i$ for selecting between the first and second inputs. The output of the bottom input multiplexer 305 is connected to another input of adder 340.

The output multiplexer 304 has a first input that is fed by zero, a second input that is connected to the output of adder 340 and is controlled by a select signal S5 for selecting between the first and second inputs. The output of the output multiplexer 304 is the output port of the output switching circuit 300.

The top output multiplexer 302 has a first input that is fed by zero, a second input that is connected to the output of adder and is controlled by a select signal S3$o$ for selecting between the first and second inputs and by an enable signal S3$e$. The output of the top output multiplexer 301 is connected to a top output switching circuit.

The bottom output multiplexer 302 has a first input that is fed by zero, a second input that is connected to the output of adder and is controlled by a select signal S4$o$ for selecting between the first and second inputs and by an enable signal S4$e$. The output of the bottom output multiplexer 301 is connected to a bottom output switching circuit.

Table 7 illustrates the control signals at various modes. Open (disconnected) is represented by 0, closed (connected) is represented by 1 and don't care is represented by x.

TABLE 7

| S3e | S3i | S3o | S4e | S4i | S4o | S5 | |
|---|---|---|---|---|---|---|---|
| 1 | 0 | 0 | 0 | 0 | 0 | 1 | Serial mode |
| 0 | 1 | X | 0 | 1 | X | 1 | Add both top and bottom |
| 1 | 0 | 1 | 0 | 1 | X | 0 | Add from top only |
| 0 | 1 | X | 1 | 0 | 1 | 0 | Add from bottom only |

Figure 8:
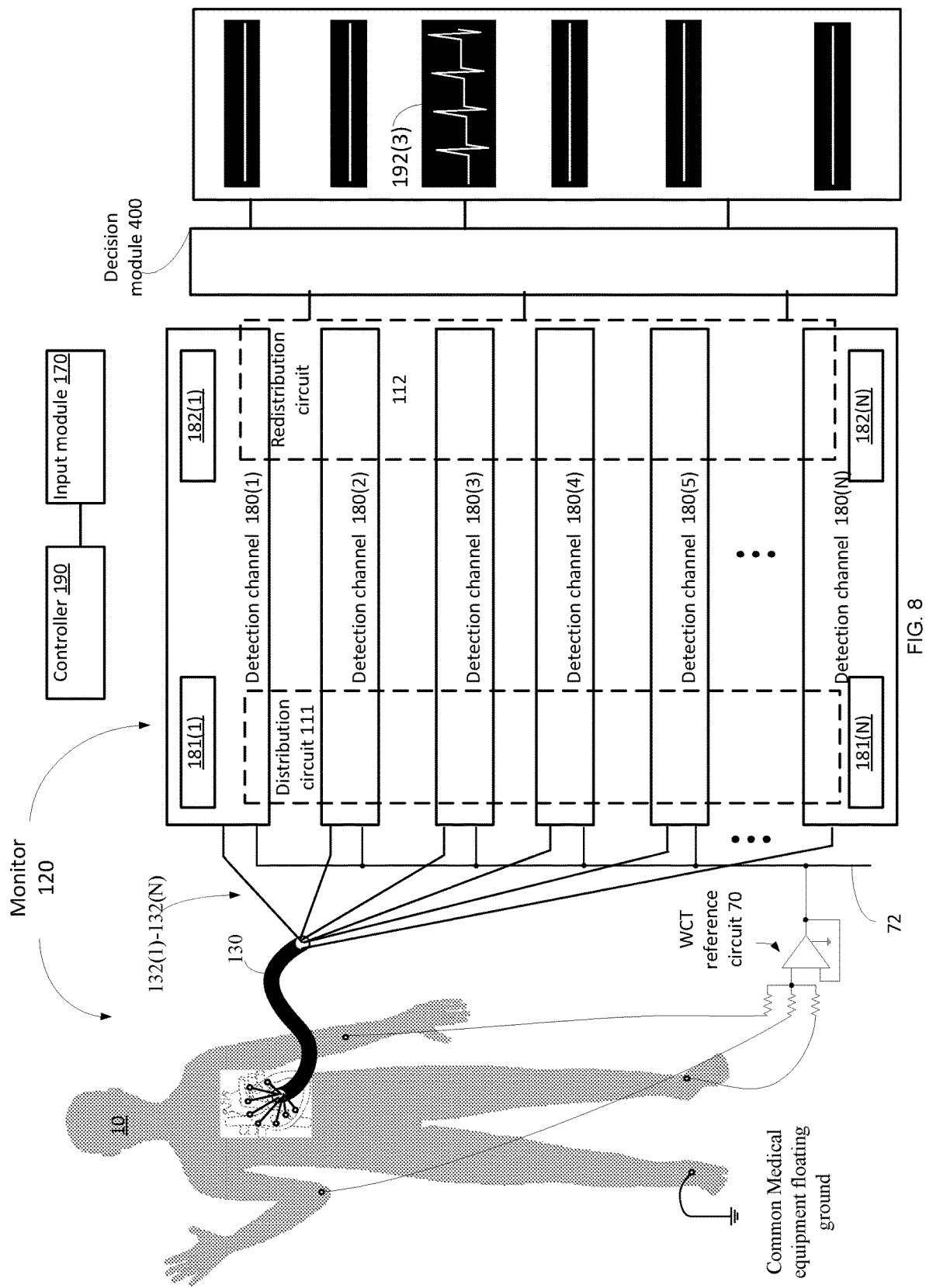
FIG. 8 illustrates a monitor according to an embodiment of the invention.

FIG. 8 illustrate monitor 120 according to an embodiment of the invention.

Monitor 120 of FIG. 8 differs from monitor of FIG. 2 by including a decision module 400 for making decisions and/o generating commands based upon the output signals of the detection channels.

The decision module 400 may translate outputs of one or more channels to commands. The decision module 400 may receive or generate a mapping between output signals of detection channels and commands.

Figure 9:
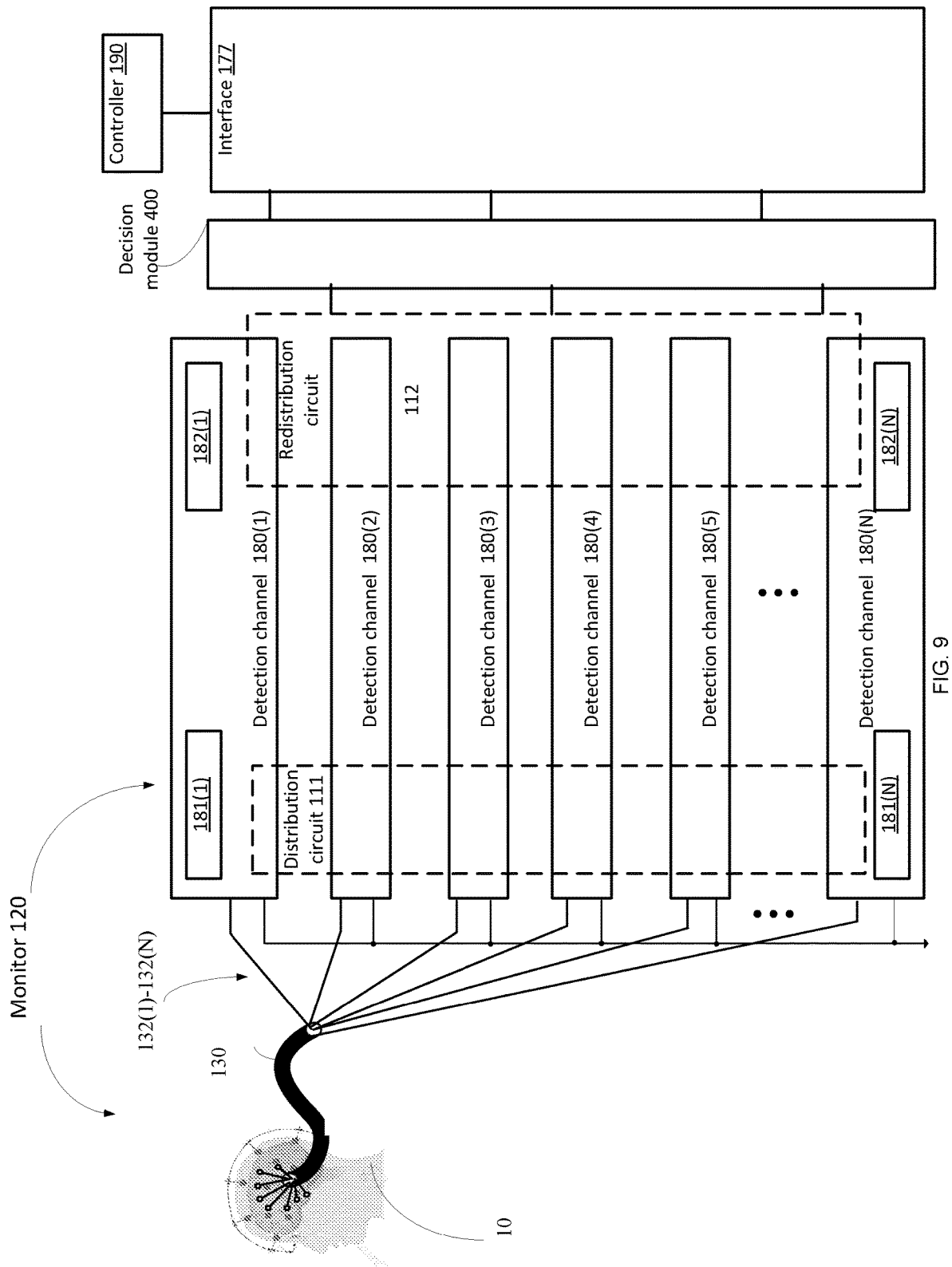
FIG. 9 illustrates a monitor according to an embodiment of the invention.

FIG. 9 illustrate monitor 120 according to an embodiment of the invention.

Monitor 120 of FIG. 9 differs from monitor of FIG. 3 by including a decision module 400 for making decisions and/o generating commands based upon the output signals of the detection channels. An additional difference is the replacement of monitor 90 and input module 170 by an output interface 177. The interface 177 may be a man machine interface (such as a display, a keyboard, a mouse), a receiver, a transmitter, and the like. Interface 177 may transmit commands to the appropriate device (for example a part of an entertainment module), receive instructions and/or information (mapping) and the like. It is noted that interface 177 may replace (or be included in addition to) the display illustrated in various other figures.

Figure 10:
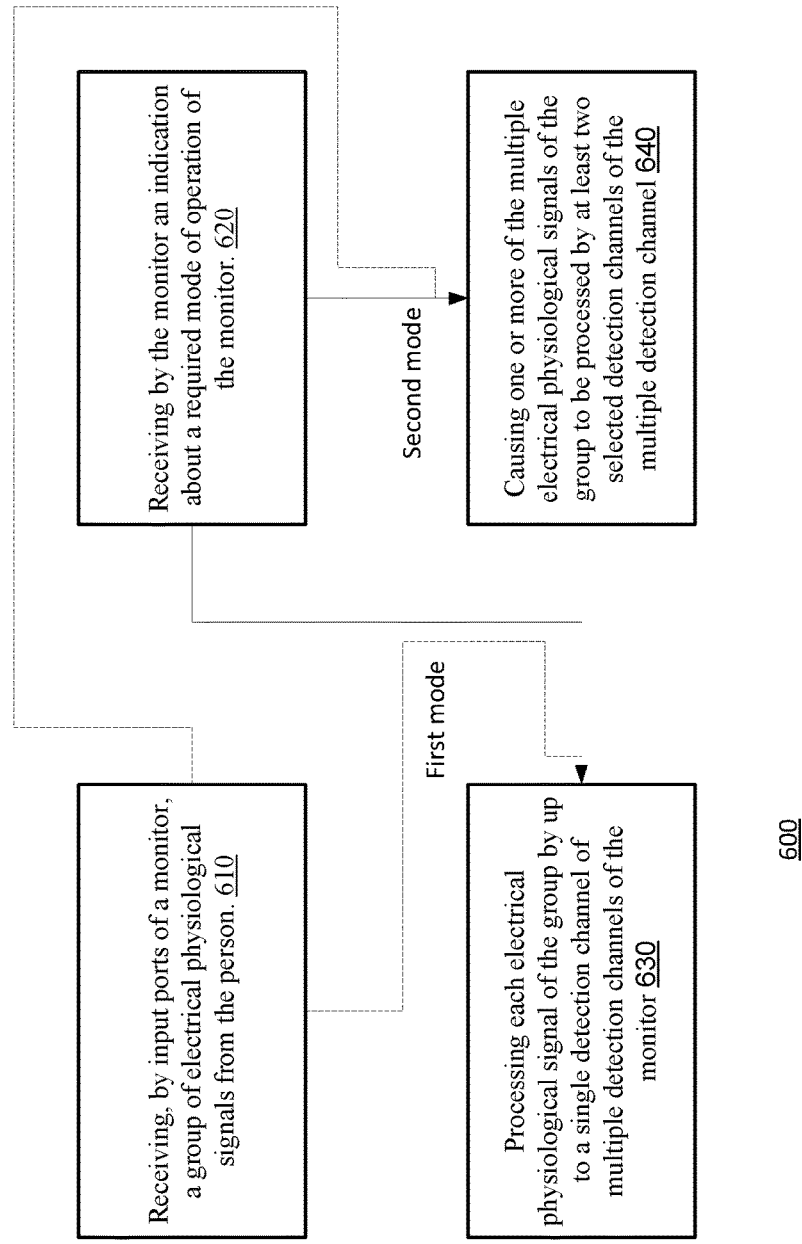
FIG. 10 illustrates a method according to an embodiment of the invention.

FIG. 10 illustrates method 600 according to an embodiment of the invention.

Method 600 starts by steps 610 and 620.

Step 610 may include receiving, by input ports of a monitor, a group of electrical physiological signals from the person.

Step 620 may include receiving by the monitor an indication about a required mode of operation of the monitor. Step 620 may be replaced by determining by the monitor the required mode. For example, the determining may be responsive to signal to noise ratio of the received electrical physiological signals or to any other property of the received electrical physiological signals and/or of expected (desired or allowed) properties of the received electrical physiological signals.

If the monitor should operate in a first mode (also referred to as serial mode) then steps 610 and 620 are followed by step 630 of processing each electrical physiological signal of the group by up to a single detection channel of multiple detection channels of the monitor. Thus—there may be idle detection channels.

If the monitor should operate in a second mode (also referred to as parallel mode or hybrid mode) then steps 610 and 620 are followed by step 640 of causing one or more of the multiple electrical physiological signals of the group to be processed by at least two selected detection channels of the multiple detection channels.

A configuration of multiple switching circuits of the monitor when the monitor operates in the first mode differs from a configuration of the multiple switching circuits of the monitor when the monitor operates in the second mode.

In a hybrid mode one or more electrical physiological signals are processed only by a single detection channel each. One or more other electrical physiological signals are processed by a plurality of detection channels each. See, for example FIG. 6.

In a fully parallel mode only one electrical physiological signal is processed—and is processed by a plurality of detection channels. See, for example, FIGS. 4 and 5.

Any combination of any components illustrated in any of the figures is provided.

Any reference to the term "comprising" or "having" should be interpreted also as referring to "consisting" of "essentially consisting of". For example—a monitor that comprises certain components can include additional components, can be limited to the certain components or may include additional components that do not materially affect the basic and novel characteristics of the monitor—respectively.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected" or "operably coupled" to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements the mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A monitor that comprises:
a controller;
conductors;
multiple detection channels having multiple first input ports for receiving, over the conductors, a group of electrical physiological signals from a person and having second input ports for receiving a reference signal;
wherein each of the channels comprises an analog conditioning circuit and an output switching circuit, wherein the analog conditioning circuit comprises:
a first radio frequency (RF) filter for filtering an electrical physiological signal received from the person to provide a first filtered RF signal;
a second RF filter for filtering the reference signal to provide a second filtered RF signal;
an input switching circuit configured to (i) receive the first filtered RF signal, the second filtered RF signal, and a top filtered RF signal that is received from an RF filter of a detection channel above the detection channel, and (ii) output two signals of the first filtered RF signal, the second filtered RF signal, and the top filtered RF signal;
a differential amplifier for receiving the two signals from the input switching circuit and amplify a difference between the two signals to provide an amplifier output signal; and
an analog low pass filter that follows the differential amplifier;
wherein multiple switching circuits of the monitor are configured according to a first configuration when the monitor operates in a first mode, thereby causing each electrical physiological signal of the group to be processed by up to a single selected detection channel of the multiple detection channels; wherein the multiple switching circuits comprise multiple input switching circuits of the multiple detection channels;
wherein the multiple switching circuits of the monitor are configured according to a second configuration when the monitor operates in a second mode thereby causing one or more of the multiple electrical physiological signals of the group to be processed by at least two selected detection channels of the multiple detection channels, wherein the controller is configured to determine when the monitor operated in the first mode and when the controller is configured to operate at the second mode.

2. The monitoring according to claim 1 wherein the switching circuits that belong to different detection channels are configured to output different electrical physiological signals when the monitor operates in the first mode; and
wherein a plurality of switching circuits that belong to a plurality of different selected detection channels are configured to output a same electrical physiological signal when the monitor operates in the second mode.

3. The monitor according to claim 2 wherein the at least two switching circuits belong to neighboring detection channels.

4. The monitor according to claim 2 wherein the at least two switching circuits belong to more than two detection channels.

5. The monitor according to claim 2 wherein the multiple switching circuits comprise the multiple input switching circuit of the multiple detection channels, and multiple output switching circuits of the multiple detection channels.

6. The monitor according to claim 2 wherein each switching circuit is a first analog component of the analog conditioning circuit.

7. The monitor according to claim 2 wherein each switching circuit is a last analog component of the analog conditioning circuit.

8. The monitor according to claim 1 wherein the multiple detection channels comprise multiple analog conditioning circuits that are followed by multiple analog to digital converters for converting multiple analog output signals of the multiple analog conditioning circuits to multiple intermediate digital signals;
wherein the multiple analog to digital converters are followed by a digital manipulator;
wherein the digital manipulator is prevented from adding intermediate digital signals from analog conditioning circuits of different selected detection channels when the monitor operates in a first mode;
wherein the digital manipulator is configured to add intermediate digital signals from analog conditioning circuits of the at least two selected detection channels when the monitor operates in the second mode.

9. The monitor according to claim 8 wherein the digital manipulator comprises a digital manipulation circuit per each detection channel; wherein each digital manipulation circuit is coupled to a set of digital to analog converters of a set of detection channels.

10. The monitor according to claim 9 wherein a digital manipulation circuit of a given detection channel that belongs to a given set of detection channels comprises:
a plurality of IO interfaces, each IO interface is coupled to a digital manipulation circuit of another detection channel of the given set;
an adder that has (a) a first input that is coupled to the analog to digital circuit of the given detection channel, (b) an IO interface for each other detection channel of the set, wherein each IO interface is coupled to a digital manipulation circuit of another detection channel of the set, and (c) an adder output;
an output circuit for outputting a digital manipulation circuit output signal;
wherein the output circuit is coupled to the adder output and to each one of the plurality of IO interfaces.

11. The monitor according to claim 8 wherein the digital manipulator is followed by a decision module for making decisions based upon output signals of the detection channels.

12. The monitor according to claim 11 wherein the display is configured to display an aggregate signal that represents an outcome of the processing each one of the one or more of the multiple electrical physiological signals by the at least two selected detection channels of the multiple detection channels.

13. The monitor according to claim 1 further comprising a display for displaying multiple output signals of the multiple detection channels.

14. The monitor according to claim 1 wherein the group of physiological signals are electrocardiogram (ECG) signals.

15. The monitor according to claim 1 wherein the group of physiological signals are electroencephalogram (EEG) signals.

16. The monitor according to claim 1 comprising a controller that is configured to determine an operational mode of the monitor.

17. A method for monitoring a person, the method comprises:
   receiving, by first input ports of a monitor, a group of electrical physiological signals from the person;
   receiving, by second input ports of the monitor, a reference signal;
   wherein the monitor operates in a first mode, processing each electrical physiological signal of the group by up to a single detection channel of multiple detection channels of the monitor;
   wherein the monitor operates in a second mode, causing one or more of the multiple electrical physiological signals of the group to be processed by at least two selected detection channels of the multiple detection channels;
   wherein a configuration of multiple switching circuits of the monitor when the monitor operates in the first mode differs from a configuration of the multiple switching circuits of the monitor when the monitor operates in the second mode, and
   wherein a processing of an electrical physiological signal of the group by a detection channel comprises:
      filtering, by a first radio frequency (RF) filter, the electrical physiological signal to provide a first filtered RF signal;
      filtering, by a second RF filter, a reference signal to provide a second filtered RF signal;
      receiving, by an input switching circuit of the multiple switching circuit, the first filtered RF signal, the second filtered RF signal, and a top filtered RF signal that is received from an RF filter of a detection channel above the detection channel;
      outputting, by an input switching circuit of the multiple switching circuit, two signals of the first filtered RF signal, the second filtered RF signal, and the top filtered RF signal;
      amplifying, by a differential amplifier, a difference between the two signals to provide an amplifier output signal;
   low pass filtering the amplifier output signal by an analog low pass filter that follows the differential amplifier; and
   performing output switching.

18. A non-transitory computer readable medium that stores instructions that once executed by a monitor cause the monitor to:
   receive, by first input ports of a monitor, a group of electrical physiological signals from a person;
   receive, by second input ports of the monitor, a reference signal;
   wherein the monitor operates in a first mode, processing each electrical physiological signal of the group by up to a single detection channel of multiple detection channels of the monitor;
   wherein the monitor operates in a second mode, causing one or more of the multiple electrical physiological signals of the group to be processed by at least two selected detection channels of the multiple detection channels;
   wherein a configuration of multiple switching circuits of the monitor when the monitor operates in the first mode differs from a configuration of the multiple switching circuits of the monitor when the monitor operates in the second mode, and
   wherein a processing of an electrical physiological signal of the group by a detection channel comprises:
      filtering, by a first radio frequency (RF) filter, the electrical physiological signal to provide a first filtered RF signal;
      filtering, by a second RF filter, a reference signal to provide a second filtered RF signal;
      receiving, by an input switching circuit of the multiple switching circuit, the first filtered RF signal, the second filtered RF signal, and a top filtered RF signal that is received from an RF filter of a detection channel above the detection channel;
      outputting, by an input switching circuit of the multiple switching circuit, two signals of the first filtered RF signal, the second filtered RF signal, and the top filtered RF signal;
      amplifying, by a differential amplifier, a difference between the two signals to provide an amplifier output signal;
   low pass filtering the amplifier output signal by an analog low pass filter that follows the differential amplifier; and
   performing output switching.

* * * * *